US00PP30227P3

(12) United States Plant Patent
Conner

(10) Patent No.: US PP30,227 P3
(45) Date of Patent: Feb. 26, 2019

(54) PECAN TREE NAMED 'GA. 00-7-75'

(50) Latin Name: *Carya illinoinensis*
Varietal Denomination: Ga. 00-7-75

(71) Applicant: University of Georgia Research Foundation, Inc., Athens, GA (US)

(72) Inventor: Patrick J. Conner, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 15 days.

(21) Appl. No.: 15/530,917

(22) Filed: Mar. 21, 2017

(65) Prior Publication Data

US 2018/0279524 P1 Sep. 27, 2018

(51) Int. Cl.
*A01H 5/08* (2018.01)
*A01H 6/00* (2018.01)

(52) U.S. Cl.
USPC ..... Plt./153
CPC ..... *A01H 6/00* (2018.05); *A01H 5/08* (2013.01)

(58) Field of Classification Search
USPC ..... Plt./153
See application file for complete search history.

*Primary Examiner* — Keith O. Robinson
(74) *Attorney, Agent, or Firm* — Klarquist Sparkman, LLP

(57) ABSTRACT

A pecan tree distinguished by the following unique combination of characteristics: Large nut size, good kernel quality, moderately early harvest date, and excellent resistance to the scab fungus (*Fusicladosporium effusum*).

4 Drawing Sheets

Latin name of the genus and species of the plant: *Carya illinoinensis.*

Variety denomination: 'Ga. 00-7-75'.

BACKGROUND OF THE INVENTION

In 2000 the cross of 'Barton' x 'Gloria Grande' was made by Patrick Conner at the University of Georgia-Tifton Campus. 'Barton' is the male pollen parent and is a 1953 USDA release which is notable for a thin shell, early harvest, and strong resistance to pecan scab [*Fusicladium effusum* (syn. *Cladosporium caryigenum*)]. 'Gloria Grande' is the female seed parent and is a selection from Orangeburg, S.C. with unknown parentage. 'Gloria Grande' was recommended for planting in Georgia for many years because of its stable and high yields and strong resistance to pecan scab. 'Barton' and 'Gloria Grande' are both unpatented cultivars. 141 nuts were collected from this cross and they produced 79 seedlings. These seedlings were grown in a seedling nursery for two years and then they were planted for observation into a seedling orchard at a farm in Tift County, Ga. One of these seedlings is identified by the cultivar name 'Ga. 00-7-75'. 'Ga. 00-7-75', a tree produced from one of the nuts of this cross, first fruited in 2007, and has fruited every year since. 'Ga. 00-7-75' was selected for trial in 2009 because of its lack of scab infection, large nut size, good kernel quality, and moderately early harvest.

BRIEF SUMMARY OF THE INVENTION

'Ga. 00-7-75' is distinguished from other pecan varieties known to the inventor due to the following unique combination of characteristics: Large nut size, good kernel quality, moderately early harvest date, and excellent resistance to the scab fungus.

Asexual reproduction of 'Ga. 00-7-75' by grafting (top working) onto 'Headquarters' (unpatented) pecan trees in 2009 to 2012 at Tifton, Ga. and whip grafting pecan seedlings at Ray City, Albany, and Attapulgus, Ga. was performed in order to evaluate these trees. Asexual reproduction of 'Ga. 00-7-75' has shown that the forgoing unique combination of characteristics come true to form, are firmly fixed, and are established and transmitted through succeeding propagations.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart, 2005. The color characteristics of this type may vary with lighting and other conditions. Therefore, color characteristics of this new variety should be determined with reference to the observations described herein, rather than from these illustrations alone.

DETAILED DESCRIPTION

Figure 2:
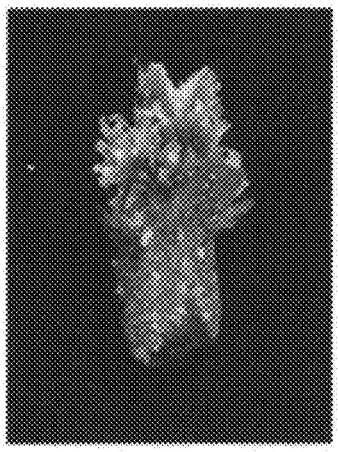
FIG. 2 is a photograph showing the form and color of the stigma of 'Ga. 00-7-75'.
Figure 3:
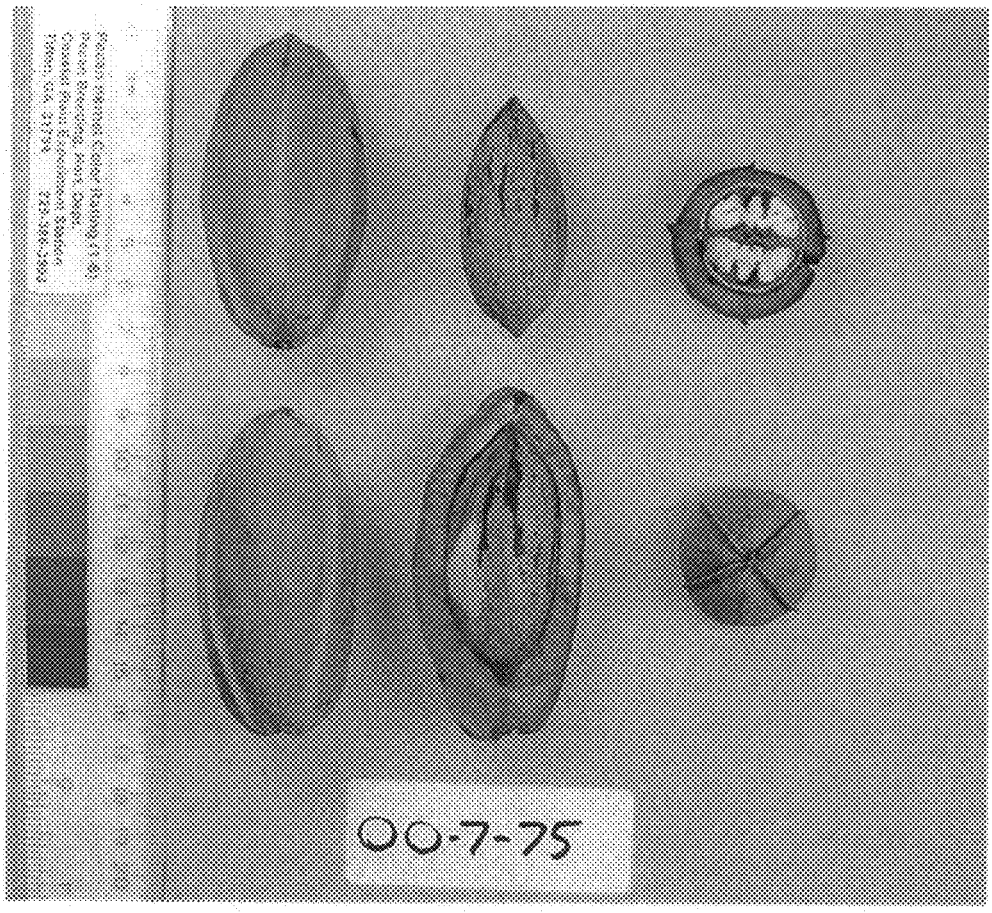
FIG. 3 is a photograph showing the nut shucks and nut of 'Ga. 00-7-75' nuts.
Figure 4:
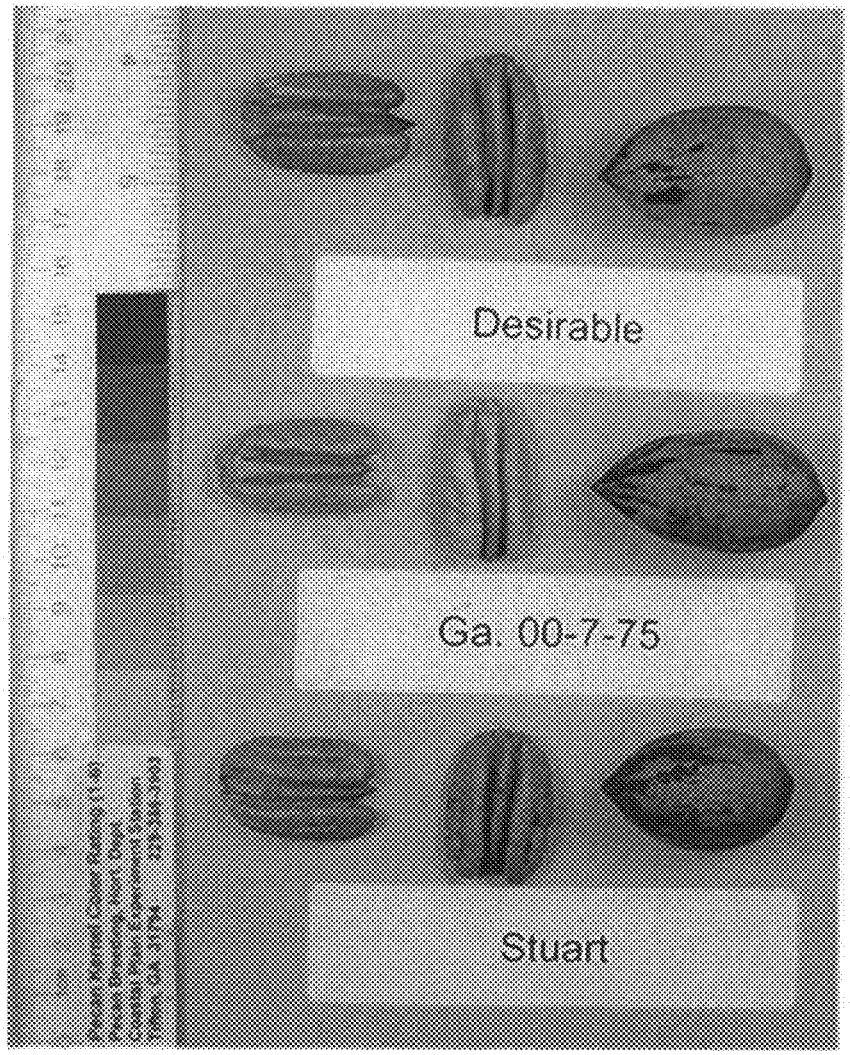
FIG. 4 is a photograph showing nut shape and kernel characteristics of 'Ga. 00-7-75' (center) in comparison to 'Desirable' (top) and 'Stuart' (bottom).

Botanical: The following detailed description of 'Ga. 00-7-75' is based on observations of the original tree at ages 14 and 15 growing in Tifton, Ga. and of asexually reproduced progeny on their first through seventh years from top-working grafts, growing in Tifton, Ray City, Albany, and Attapulgus, Ga. FIGS. 2, 3 and 4 are from the 14 year old original tree. The description is based on the original tree at age 15; except for the pollen shed and pistil receptivity, and comparisons to other cultivars which were based on six grafted trees on their first through seventh year from top-working grafts.

*Varietal name*.—'Ga. 00-7-75'.

*Parentage*.—Seed parent: 'Gloria Grande'. Pollen parent: 'Barton'.

*Description of plant material*.—

*Tree*.—'Ga. 00-7-75' trees are vigorous growers with an upright growing canopy. Trunks are scaly and brown in color (RHS N200C). Leaves are dark green (RHS 137A) on the adaxial side and lighter in color on the abaxial side (RHS 137C). Leaf and leaflet size and shape vary within the canopy and are not suitable for cultivar identification. The 'Ga. 00-7-75' trees have a dense branching pattern.

*Leaves*.—The mature leaf is odd pinnate compound. Each mature leaf has 9 to 17 leaflets. Size of mature leaves (fourth leaf from base of shoot) is 36 to 53 cm long and 22 to 30 cm wide. Leaflets are falcate in shape. Fourth leaflet on fourth leaf is 2.5 to 5.5 cm wide and 13 to 16 cm long. The petiolule of the fourth leaflet of the fourth leaf is 3 mm long and 1.5 mm wide and yellow-green (RHS 146C) in color. Leaf (bud) burst is late, averaging April 5 in Tifton, Ga. as shown in Table 8. Time of leaf fall is late Autumn, typically December 4, but very dependent upon yearly weather.

Figure 1:
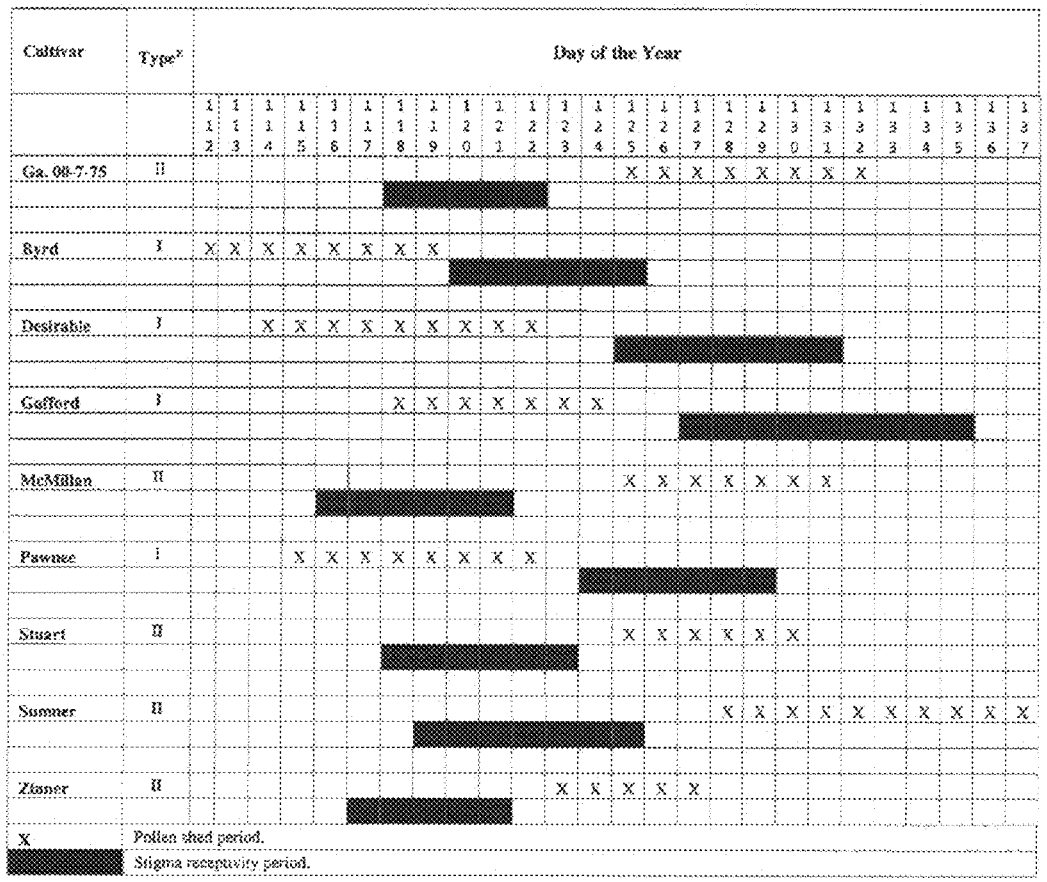
FIG. 1 is a pollination chart showing the timing of pollen shed and stigma receptivity of 'Ga. 00-7-75' in comparison to several other pecan cultivars grown in Tifton, Ga.

*Flower*.—'Ga. 00-7-75' is protogynous in flowering (type II) with midseason receptivity and mid to late season pollen shed (FIG. 1). It would be pollinated by 'Byrd' (U.S. Plant Pat. No. 20,867, 'Desirable' (unpatented), 'Gafford' (unpatented), and 'Pawnee' (unpatented). It would pollinate 'Desirable', 'Gafford', and 'Pawnee'. The stigma is small, upright with small lobes, and yellow-green (RHS 145A) (FIG. 2). The stigma is typically 5.1 mm long and 2.3 mm wide. Splitting of the stigma is weak. Anthocyanin coloration of the stigma is absent. Determinant pendulous catkin. Typical length of catkin is 120 mm and typical width is 4 mm.

*Nut in shuck*.—Topography is smooth and shuck texture is rough (FIG. 3). Shuck suture wings are relatively small (2-3 mm in height). Typically only 1 shuck has a russet stripe which runs from the base to the apex and is 1.5-2.0 mm in thickness. Shuck color is whitish green (RHS 146C) and is lighter in color than most cultivars. Shuck apex is obtuse. Light shuck color and rough texture are the most useful identification traits for this cultivar. Shucks are not persistent after nut fall. Typical time of 50% shuck opening is October 4 as given in Table 8. Ribs of the husk are medium in prominence.

*Dry nut*.—Nut shells have moderate shell striping which extends from the apex to the equator (FIG. 3). Dots are small and present from base to apex. The dots are 0.5 to 2.5 mm in diameter and are dark brown (RHS 200A). Nut shape is oblong with a cuspidate base and an acute, grooved apex. Nuts are round in cross section. Shell topography is slightly bumpy with ridges from the base to the apex. Shell thickness is medium and 0.8-1.0 mm thick at the equator. Nuts of 'Ga. 00-7-75' average 51 mm in length and 23 mm in width, with a 5 mm tip. Nuts are grey-brown (RHS 199C) in color. Kernel size of the nut is large. Typical weight of the kernel is 5.3 g.

Comparisons to other varieties:

*Comparison to parents*.—In comparison to 'Barton', 'Ga. 00-7-75' has a larger nut. 'Ga. 00-7-75' has a typical nut size of 9.9 g while 'Barton' has a typical nut size of 6.8 g. In comparison to 'Gloria Grande', 'Ga. 00-7-75' has a higher percentage kernel. 'Ga. 00-7-75' typically has a 53.7% kernel while 'Gloria Grande' typically has a 45% kernel.

*Scab resistance*.—'Ga. 00-7-75' has shown very strong resistance to pecan scab in replicated tests. Trees have been grown in a sprayed orchard at Tifton, Ga. since 2009, and at Ray City, Ga. since 2012 and no scab infection has been observed on any of these trees on leaves or nuts (Tables 1, 2). In comparison, susceptible cultivars like 'Desirable' and 'Byrd' had significant scab infection. High pressure, unsprayed trials were conducted at Tifton, Ga. and in these trials only slight scab was seen on a few nuts (Table 3). This disease incidence was not different from the highly resistant controls ('Elliott' (unpatented), 'Gafford', and 'McMillan' (unpatented)), and was better than moderately resistant controls ('Sumner' (unpatented) and 'Zinner' (unpatented)). Susceptible controls such as 'Cunard' (U.S. Plant Pat. No. 24,373), 'Desirable', 'Pawnee' and 'Stuart' (unpatented) experienced crop failure and defoliation each year due to scab infection. Young trees were also planted in unsprayed scab screening orchards in Attapulgus, Ga. and Albany, Ga. While they have not fruited yet, leaf scab resistance of 'Ga. 00-7-75' was similar to resistant controls and better than susceptible controls (Tables 3, 4, 5).

*Production*.—To evaluate yield, 'Ga. 00-7-75' was topworked into a bearing orchard at a farm in Tift County, Ga. Using this method, 'Ga. 00-7-75' appears to be a good yielding tree with yields steadily increasing each year (Table 6). Cluster size of 'Ga. 00-7-75' is 2.6, which is similar to other cultivars with stable bearing habits ('Desirable', 'Stuart', and 'Zinner') and less than alternating cultivars that need crop thinning ('Byrd', 'McMillan', 'Pawnee', and 'Sumner'). Moderate cluster size, along with the mother tree's consistent cropping record (9 years with 50% or more of a crop), indicate that 'Ga. 00-7-75' will not need to be crop thinned.

*Nut quality*.—Nut size (9.9 g) and percent kernel (53.7%) fall within the range needed for optimum prices in the current market (Table 7). Shellers generally want nut size to be larger than 9 g and more than 52% kernel for shipping to the Chinese market. 'Ga. 00-7-75' has similar size to 'Desirable' and a higher percent kernel (Table 7). Additionally, 'Ga. 00-7-75' has little incidence of packing material sticking to the kernel and highly attractive kernels (Table 7).

*Adaptation.*—'Ga. 00-7-75' is late to break bud in the spring (Table 8) which indicates some measure of frost avoidance if planted in the northern part of Georgia. For many years 'Stuart' was recommended for north Georgia, and budbreak of 'Ga. 00-7-75' is similar to 'Stuart'. Harvest date is almost a week ahead of 'Desirable' (Table 8) which puts it in the early mid-season harvest period. This would make 'Ga. 00-7-75' among the first cultivars to be harvested, but not so early that extra protection from predators like crows would be necessary. 'Ga. 00-7-75' has medium susceptibility to black pecan aphid (*Melanocallis caryaefoliae*) which may require sprays in some years, but susceptibility is less than other widely grown cultivars such as 'Zinner' and 'Stuart' (Tables 1, 2, 3, 4).

TABLE 1

Pest resistance of pecan cultivars and selections in a sprayed orchard over years 2009-2015 at Tifton, GA. Of the varieties other than 'Ga. 00-7-75' in Table 1, only 'Byrd' (U.S. Plant Pat. No.20,867) is patented.

| Cultivar | # Trees | Leaf scab[Z] | Avg. nut scab[Y] | Max. nut scab[X] | Black aphid damage[W] |
|---|---|---|---|---|---|
| 'Ga. 00-7-75' | 6 | 1.0 b[V] | 1.0 b | 1.0 d | 2.3 bc |
| 'Byrd' | 5 | 1.1 b | 1.3 b | 2.9 b | 1.5 d |
| 'Desirable' | 6 | 3.7 a | 3.4 a | 4.6 a | 2.2 bc |
| 'Gafford' | 4 | 1.0 b | 1.0 b | 1.0 d | 1.0 e |
| 'McMillan' | 5 | 1.0 b | 1.0 b | 1.1 d | 1.6 d |
| 'Pawnee' | 3 | 1.2 b | 1.0 b | 1.9 c | 1.7 d |
| 'Stuart' | 5 | 1.0 b | 1.1 b | 3.1 b | 2.6 b |
| 'Sumner' | 4 | 1.3 b | 1.0 b | 1.1 d | 2.1 c |
| 'Zinner' | 6 | 1.3 b | 1.1 b | 2.9 b | 3.1 a |
| Sig. | | 0.001 | 0.001 | 0.001 | 0.001 |

[Z]1 = no scab lesions, 2 = a few isolated lesions with restricted growth, 3 = multiple lesions with expanding lesions, 4 = stem scab lesions or defoliation.
[Y]1 = no scab lesions, 2 = a few lesions with restricted growth, 3 = multiple lesions, 0% to 10% coverage, 4 = 11% to 50% coverage, 5 = 51% to 100% coverage or nut drop. Average damage seen on nuts over the tree.
[X]1 = no scab lesions, 2 = a few lesions with restricted growth, 3 = multiple lesions, 0% to 10% coverage, 4 = 11% to 50% coverage, 5 = 51% to 100% coverage or nut drop. Maximum damage seen on any nut.
[W]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.
[V]Mean separation within a column by Duncan's multiple range test, P ≤ 0.05.

TABLE 2

Pest resistance of pecan cultivars and selections in a sprayed orchard over years 2012-2015 at Ray City, GA. 'Amling', 'Desirable', 'Elliot', 'McMillan' and 'Zinner' are all unpatented.

| Cultivar | # Trees | Leaf scab[Z] | Avg. nut scab[Y] | Max. nut scab[X] | Black aphid damage[W] |
|---|---|---|---|---|---|
| 'Ga. 00-7-75' | 6 | 1.0 b[V] | 1.0 b | 1.0 c | 1.0 b |
| 'Amling' | 6 | 1.0 b | 1.0 b | 1.0 c | 1.0 b |
| 'Desirable' | 6 | 3.5 a | 3.8 a | 4.9 a | 1.0 b |
| 'Elliott' | 6 | 1.0 b | 1.0 b | 1.0 c | 1.0 b |
| 'McMillan' | 6 | 1.0 b | 1.0 b | 1.0 c | 1.0 b |

TABLE 2-continued

Pest resistance of pecan cultivars and selections in a sprayed orchard over years 2012-2015 at Ray City, GA. 'Amling', 'Desirable', 'Elliot', 'McMillan' and 'Zinner' are all unpatented.

| Cultivar | # Trees | Leaf scab[Z] | Avg. nut scab[Y] | Max. nut scab[X] | Black aphid damage[W] |
|---|---|---|---|---|---|
| 'Zinner' | 6 | 1.0 b | 1.2 b | 2.2 b | 1.3 a |
| Sig. | | 0.001 | 0.001 | 0.001 | 0.001 |

[Z]1 = no scab lesions, 2 = a few isolated lesions with restricted growth, 3 = multiple lesions with expanding lesions, 4 = stem scab lesions or defoliation.
[Y]1 = no scab lesions, 2 = a few lesions with restricted growth, 3 = multiple lesions, 0% to 10% coverage, 4 = 11% to 50% coverage, 5 = 51% to 100% coverage or nut drop. Average damage seen on nuts over the tree.
[X]1 = no scab lesions, 2 = a few lesions with restricted growth, 3 = multiple lesions, 0% to 10% coverage, 4 = 11% to 50% coverage, 5 = 51% to 100% coverage or nut drop. Maximum damage seen on any nut.
[W]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.
[V]Mean separation within a column by Duncan's multiple range test, P ≤ 0.05.

TABLE 3

Pest resistance of pecan cultivars and selections in an unsprayed orchard over years 2012-2015 at Tifton, GA. Of the varieties other than 'Ga. 00-7-75' in Table 3, only 'Cunard' (U.S. Plant Pat. No. 24,373) is patented.

| Cultivar | # Trees | Leaf scab[Z] | Avg. nut scab[Y] | Max. nut scab[X] | Black aphid damage[W] |
|---|---|---|---|---|---|
| 'Ga. 00-7-75' | 3 | 1.0 c[V] | 1.0 c | 1.3 c | 2.6 bc |
| 'Cunard' | 1 | 3.3 ab | 4.7 a | 5.0 a | 2.3 bc |
| 'Desirable' | 1 | 4.0 a | 5.0 a | 5.0 a | 2.5 bc |
| 'Elliott' | 1 | 1.0 c | 1.0 c | 1.0 c | 2.3 c |
| 'Gafford' | 1 | 1.0 c | 1.0 c | 1.0 c | 2.0 c |
| 'McMillan' | 1 | 1.0 c | 1.0 c | 1.5 c | 2.0 c |
| 'Pawnee' | 1 | 2.3 bc | 5.0 a | 5.0 a | 2.8 abc |
| 'Stuart' | 1 | 2.5 bc | 5.0 a | 4.3 a | 3.8 a |
| 'Sumner' | 2 | 2.1 bc | 2.0 b | 3.0 b | 2.7 bc |
| 'Zinner' | 2 | 2.1 bc | 4.5 a | 4.0 a | 3.4 ab |
| Sig. | | 0.001 | 0.001 | 0.001 | 0.007 |

[Z]1 = no scab lesions, 2 = a few isolated lesions with restricted growth, 3 = multiple lesions with expanding lesions, 4 = stem scab lesions or defoliation.
[Y]1 = no scab lesions, 2 = a few lesions with restricted growth, 3 = multiple lesions, 0% to 10% coverage, 4 = 11% to 50% coverage, 5 = 51% to 100% coverage or nut drop. Average damage seen on nuts over the tree.
[X]1 = no scab lesions, 2 = a few lesions with restricted growth, 3 = multiple lesions, 0% to 10% coverage, 4 = 11% to 50% coverage, 5 = 51% to 100% coverage or nut drop. Maximum damage seen on any nut.
[W]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.
[V]Mean separation within a column by Duncan's multiple range test, P ≤ 0.05. Years were treated as reps.

TABLE 4

Pest resistance of pecan cultivars and selections in an unsprayed orchard over years 2012-2015 at Albany, GA. The patent status of the varieties in Table 4 has been set forth above.

| Cultivar | # Trees | Leaf scab[Z] | Black aphid damage[Y] |
|---|---|---|---|
| 'Ga. 00-7-75' | 3 | 1.3 b[X] | 2.2 |
| 'Byrd' | 2 | 4.0 a | 1.6 |
| 'Cunard' | 2 | 4.0 a | 2.0 |
| 'Desirable' | 3 | 4.0 a | 2.4 |
| 'Elliott' | 3 | 1.0 b | 1.4 |
| 'Sumner' | 3 | 1.7 b | 1.9 |
| Sig. | | 0.001 | NS |

[Z]1 = no scab lesions, 2 = a few isolated lesions with restricted growth, 3 = multiple lesions with expanding lesions, 4 = stem scab lesions or defoliation.
[Y]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.
[X]Mean separation within a column by Duncan's multiple range test, P ≤ 0.05.

TABLE 5

Pest resistance of pecan cultivars and selections in an unsprayed orchard over years 2012-2015 at Attapulgus, GA. The patent status of the varieties in Table 5 has been set forth above.

| Cultivar | # Trees | Leaf scab[Z] | Black aphid damage[Y] |
|---|---|---|---|
| 'Ga. 00-7-75' | 3 | 1.3 c[X] | 2.0 |
| 'Desirable' | 3 | 4.0 a | 2.2 |
| 'Elliott' | 3 | 1.5 c | 2.1 |
| 'Stuart' | 3 | 3.3 b | 2.6 |
| Sig. | | 0.001 | NS |

[Z]1 = no scab lesions, 2 = a few isolated lesions with restricted growth, 3 = multiple lesions with expanding lesions, 4 = stem scab lesions or defoliation.
[Y]1 = no damage, 2 = light chlorotic spotting, 0% to 25% leaves affected, 3 = moderate chlorotic spotting, 26% to 75% chlorotic spotting, 4 = heavy chlorotic spotting, 76% to 100% leaves affected.
[X]Mean separation within a column by Duncan's multiple range test, P ≤ 0.05.

TABLE 6

In-shell nut yield (lbs. per tree) of pecan cultivars in Tifton, GA., years 7-10 from planting. The patent status of the varieties in Table 6 has been set forth above.

| Cultivar | # Trees | Year 7 | Year 8 | Year 9 | Year 10 |
|---|---|---|---|---|---|
| 'Ga. 00-7-75[Z]' | 6 | 17.3 | 24.7 b[Y] | 47.2 ab | 77.7 b |
| 'Byrd' | 5 | 42.0 | 46.4 a | 49.7 ab | 106.5 a |
| 'Desirable' | 4 | 15.9 | 28.5 ab | 29.5 b | 36.5 c |
| 'Gafford' | 4 | 26.7 | 40.0 ab | 30.8 b | 62.5 b |
| 'Pawnee' | 3 | 15.7 | 19.3 b | 57.0 ab | 12.0 c |
| 'Sumner' | 4 | 26.8 | 25.3 b | 69.8 a | 33.2 c |
| Sig. | | NS | 0.045 | 0.04 | 0.001 |

[Z]'Ga. 00-7-75' was topworked into the orchard and when yields were similar to year 7 yields they were considered to be 7 years old.
[Y]Mean separation within a column by Duncan's multiple range test, P ≤ 0.05.

TABLE 7

Nut and kernel quality attributes of pecan cultivars averaged over all years of testing at Tifton, GA. A minimum of 4 and a maximum of 11 crops were evaluated for each tree. The patent status of the varieties in TABLE 7 has been set forth above.

| Cultivar | # Trees | # Nuts per cluster | Nut weight (g) | % Kernel | % Fuzz[Z] | Kernel rating[Y] |
|---|---|---|---|---|---|---|
| 'Ga. 00-7-75' | 6 | 2.6 b[X] | 9.9 c | 53.7 c | 0.0 d | 4.8 a |
| 'Byrd' | 5 | 3.5 a | 9.4 c | 58.0 a | 1.0 d | 4.3 b |

TABLE 7-continued

Nut and kernel quality attributes of pecan cultivars averaged over all years of testing at Tifton, GA. A minimum of 4 and a maximum of 11 crops were evaluated for each tree. The patent status of the varieties in TABLE 7 has been set forth above.

| Cultivar | # Trees | # Nuts per cluster | Nut weight (g) | % Kernel | % Fuzz[Z] | Kernel rating[Y] |
|---|---|---|---|---|---|---|
| 'Desirable' | 6 | 2.4 b | 9.9 c | 50.9 de | 2.3 c | 3.6 c |
| 'Gafford' | 4 | 2.7 b | 9.3 bc | 50.2 e | 3.8 b | 3.7 c |
| 'McMillan' | 5 | 3.3 a | 8.9 ab | 51.4 de | 0.3 d | 3.6 c |
| 'Pawnee' | 3 | 3.5 a | 9.9 c | 57.2 ab | 0.0 d | 3.9 bc |
| 'Stuart' | 5 | 2.6 b | 9.6 c | 45.4 f | 7.7 a | 2.2 d |
| 'Sumner' | 4 | 3.6 a | 8.4 a | 52.0 d | 2.4 c | 3.8 c |
| 'Zinner' | 6 | 2.6 b | 9.9 c | 56.4 b | 0.2 d | 4.9 a |
| Sig. | | 0.001 | 0.001 | 0.001 | 0.001 | 0.001 |

[Z]Estimated percentage of the kernel surface covered with packing material.
[Y]Attractiveness rating of the pecan kernels with 5 = Excellent, 4 = Good, 3 = Average, 2 = Poor, 1 = Terrible. Ratings are based on kernel color, size, fill, shelling ability, and lack of defects.
[X]Mean separation within a column by Duncan's multiple range test, P ≤ 0.05.

TABLE 8

Phenology and number of nuts per cluster of pecan cultivars in Tifton, GA., 2008-2015. The patent status of the varieties in Table 8 has been set forth above.

| Cultivar | # Trees | Bud burst date | # Nuts per cluster | 50% Shuck split date |
|---|---|---|---|---|
| 'Ga. 00-7-75' | 6 | 6-Apr a[Z] | 2.6 b | 4-Oct c |
| 'Byrd' | 5 | 26-Mar d | 3.5a | 18-Sep d |
| 'Desirable' | 6 | 30-Mar c | 2.4 b | 10-Oct ab |
| 'Gafford' | 4 | 6-Apr a | 2.7b | 10-Oct ab |
| 'McMillan' | 5 | 31-Mar bc | 3.3 a | 6-Oct bc |
| 'Pawnee' | 3 | 31-Mar bc | 3.5 a | 9-Sep e |
| 'Stuart' | 5 | 3-Apr ab | 2.6b | 11-Oct a |
| 'Sumner' | 4 | 31-Mar bc | 3.6a | 9-Oct b |
| 'Zinner' | 6 | 1-Apr bc | 2.6 b | 5-Oct c |
| Sig. | | 0.001 | 0.001 | 0.001 |

[Z]Mean separation within a column by Duncan's multiple range test, P ≤ 0.05.

The 'Ga. 00-7-75' pecan tree is therefore an improved new and distinct pecan.

I claim:

1. A new and distinct cultivar of pecan tree, as herein illustrated and described.

* * * * *

Pollination chart for pecan cultivars in Tifton, Ga.

[z]Type I = protandrous, Type II = protogynous.